United States Patent [19]

Thompson

[11] 4,002,667
[45] Jan. 11, 1977

[54] BIS-(2-HYDROXYETHYL)-TEREPHTHALATE

[75] Inventor: John Martin Thompson, Manchester, England

[73] Assignee: Imperial Chemical Industries, Limited, London, England

[22] Filed: Mar. 17, 1975

[21] Appl. No.: 558,694

[30] Foreign Application Priority Data

Mar. 26, 1974 United Kingdom ............ 13277/74

[52] U.S. Cl. ............................................. 260/475 P
[51] Int. Cl.$^2$ ...................................... C07C 69/82
[58] Field of Search ............................... 260/475 P

[56] References Cited

FOREIGN PATENTS OR APPLICATIONS 47-7781    6/1972    Japan ........................... 260/475 P

*Primary Examiner*—Jane S. Myers
*Attorney, Agent, or Firm*—Cushman, Darby & Cushman

[57] ABSTRACT

A process for the manufacture of bis-(2-hydroxyethyl)-terephthalate which comprises heating together dimethyl terephthalate and a substantial excess of ethylene glycol in the presence of a basic ester interchange catalyst, under reduced pressure whereby the by-product methanol is distilled out of the system. This process enables bis(2-hydroxyethyl)-terephthalate of good quality to be made in improved yield and with minimal oligomer formation compared with previously known methods. The product finds application in the manufacture of polymers such as poly (ethylene terephthalate).

7 Claims, No Drawings

BIS-(2-HYDROXYETHYL)-TEREPHTHALATE

This invention relates to a process for the manufacture of bis-(2-hydroxyethyl)-terephthalate by an ester-interchange reaction between dimethyl terephthalate and ethylene glycol.

Bis-(2-hydroxyethyl)-terephthalate is known to be made by ester-interchange between ethylene glycol and dimethyl terephthalate in the presence of a variety of catalysts including the acetates of calcium, zinc and manganese. The ester-interchange reaction normally starts at about 140°–150° C, methanol is distilled out of the system and the reaction mass temperature is slowly raised to about 200° C to complete reaction. In addition to the required bis-ester, varying proportins of oligomeric by-products are formed during the reaction which reduce the yield and complicate the recovery of the required bis-ester.

The relative proportions of oligomeric by-products formed depend on the catalyst, temperature and molar ratio of dimethyl terephthalate to ethylene glycol and if large amounts of by-product are formed recovery of the pure bis-(hydroxyethyl) ester becomes more difficult We have found that traces of acidic materials normally present in ethylene glycol or dimethyl terephthalate used as starting materials have a profound effect on the reaction and we have found that if this acidic material is neutralised with a base and a small amount of excess base over that required for neutralisation added, the reaction can be carried out at must lower temperatures under reduced pressure to give good yields of the monomeric bis-(2-hydroxyethyl) ester. We have found that under these conditions the reaction can be carried out at pressures of from 15 mms. to 100 mms. of Hg and the reaction can be completed at temperatures of the order of 105° to 125° depending on the pressure used.

In contrast, using the normal fibre-forming grades of ester and glycol with a manganese acetate catalyst, ethylene glycol tends to distil from the reaction mixture at about 105° C. at 22 mms. of Hg before any signs of reaction have occurred even when up to ten times the normal amount of manganese acetate is used. In order to obtain a low pressure process with manganese acetate it is necessary to use starting materials of an even higher grade of purity than those purified materials normally used for fibre manufacture.

Thus according to the present invention there is provided a process for the manufacture of bis-(2-hydroxyethyl)-terephthalate which comprises heating together dimethyl terephthalate and ethylene glycol under distillation conditions at a pressure of from 15 mms. to 100 mms. Hg in the presence of a basic catalyst in excess over that required to neutralise any acidity in the dimethyl terephthalate or ethylene glycol.

We prefer to use a molar ratio of ethylene glycol to dimethyl terephthalate of at least 8:1 preferably from 8:1 to 10:1. Although ratios outside these limits may be used, a ratio of above 10 to 1 is not necessarily economically advantageous and ratios below 8 to 1 lead to increased oligomer formation with consequent difficulty in recovery of the desired monomeric bis-ester.

In carrying out the reaction the reactants and catalyst are mixed together and heated at a pressure of from 15 to 100 mms. of Hg. At a pressure of 15 mms. Hg for example reaction begins at about 50°-60° C. with distillation of methanol and is complete at 105°-125° C. when ethylene glycol begins to distil over. On the completion of the reaction the product may be isolated by pouring the reaction mixture into water, separating the hot aqueous liquor from insolubles for example, by filtration, and allowing the product to crystallise.

The reaction is carried out under distillation conditions, that is the reaction vessel is provided with a distillation head and means for condensing the methanol evolved. It is preferred that the distillation head consist of a packed distillation column in order to assist separation of methanol and ethylene glycol which latter may otherwise be entrained and carried off with the methanol.

If an ethylene glycol to dimethyl terephthalate ratio of less than 8:1 is used, oligomer formation increases rapidly and its removal can cause trouble, although oligomer once recovered can be charged to a further preparation.

If an ethylene glycol to dimethyl terephthalate ratio above 10:1 is used the value of the increased yeidl only matches the extra cost if the excess glycol can be recovered and re-used. This is achieved using a slightly modified process which is exemplified in Examples 23A and B. In this case the bis-(2-hydroxyethyl)ester is allowed to crystallise from the reaction liquid without a preliminary discharge into an aqueous medium and is separated, for example, by filtration, from the mother liquor which may then be used in another preparation. Additional base must be used in such later preparation in order to allow for terephthalic acid formed in small quantity in the earlier preparation and present in the recovered ethylene glycol. The purity of the bis-ester produced by this total isolation procedure is normally satisfactory, the proportion of oligomer being small on account of the high ethylene glycol/dimethyl terephthalate ratio.

Preferred bases for use in the process of the invention are the alkali and alkaline earth metals or their oxides, hydroxides, stable bicarbonates, carbonates and alcoholates. The metals are included as basic catalysts because on adding to the ethylene glycol they form the metal glycoloxide or glycolate which acts as catalyst. Specific examples of such catalysts include sodium hydroxide, potassium hydroxide, potassium carbonate, calcium oxide, sodium which acts as the glycoloxide and sodium bicarbonate. Certain alkaline salts such as disodium hydrogen phosphate and strong organic bases for example quaternary ammonium hydroxide such as benzyl trimethylammonium hydroxide may also be used as catalysts.

The acidity in the starting materials in the present process largely comprises terephthalic acid present in the dimethyl terephthalate and the acidity in the starting materials can be determined by standard methods. The quantity of base required in the present process is an excess over that required to neutralise any acidity in the ethylene glycol or dimethyl terephthalate. The amount of excess base catalyst required is in fact very small, in practice on the manufacturing side however it has been found best to use a total amount of base, both for catalytic and neutralisation purposes, of from 0.025 to 1.0% by weight of the dimethyl terephthalate preferably from 0.2 to 0.3% thus allowing for variations in the acidity of the starting materials without having to analyse each separate container. This amount of base may in fact be of the order of 8 times that used to neutralise the acidity if the acidity is very small. Too large an excess is to be avoided in order to minimise oligomer formation.

The product may be used for the manufacture of polymers such as poly-(ethylene terephthalate).

By the present process it is possible to make bis-(2-hydroxyethyl)-terephthalate in improved yield and of good quality with minimal oligomer formation.

The invention is illustrated by the following examples in which all parts and percentages are by weight except where otherwise stated. Where parts by volume are given the relationship to weight is that of the millilitre to the gram.

Example 1

A mixture of dimethyl terephthalate (194 parts), ethylene glycol (496 parts) and sodium carbonate (0.125 part) is placed in a 1 litre reaction flask fitted with a stirrer and a small fractionating column, packed for a length of 6 with Lessing rings, leading to a condenser system capable of being cooled by circulating either a suitable heat transfer liquid cooled by solid carbon dioxide or ice-salt brine. The mixture is heated under a vacuum of 56 mm. approximately. Methanol begins to distil rapidly from the system at 78° C and the reaction is complete in about 45 minutes by which time the reaction solution temperature has reached a temperature of 123° C. approximately and ethylene glycol is just beginning to distil with a column head temperature of 120° C. approximately. The yield of methanol is virtually theoretical (64 parts).

The reaction product is poured immediately into water (1100 parts by volume) containing as suitable filter aid Hyflo Supercel (3.5 parts) and the temperature is adjusted to 90°–95° C. After stirring the mixture at this temperature for 2 – 3 hours it is screened through a suitable medium contained in a steam-heated vacuum nutsche. The clear filtrate is allowed to cool with stirring to 20° C and the product is isolated by vacuum filtration. The filter-cake is washed, to remove excess ethylene glycol, with water (3 × 300 parts by volume) and then dried in an oven at 55°–60° C. The yield of bis-(2-hydroxyethyl)-terephthalate is 219 parts (86.2%) m.pt. 108.8°– 109.8° C which is sufficiently pure for most purposes requiring pure bis-(2-hydroxyethyl)-terephthalate. The oligomer residue weighs 17 parts approximately inclusive of filter-aid.

The invention is further exemplified by the results, given in Table 1, of experiments carried out in a similar manner, but with the differences noted, to that described in Example 1.

Examples 2 – 4A and 18 – 20A show the effect of different basic catalysts.

Examples 5 – 8 show the effect of adding oligomeric residues from a previous preparation, in this case, Example 1.

Examples 9 – 11 show the effect of different basic catalysts together with different temperatures of screening the oligomer residues.

Examples 12 – 14 shows the effect of acids on the "normal" EI reaction and the effect of base on such acidified rection mixtures.

Examples 15 – 17 A are for purposes of comparing the performance of a typical EI reaction catalyst such as manganese acetate with the bases used in this invention to neutralise the catalyst deactivating acidic impurities.

TABLE I

| Example No. | DMT Wt. parts | EG Wt. parts | Catalyst parts | mm Hg. Vacuum | Temperature of start of reaction ° C | Maximum temp. of reaction mixture ° C | Drown-out mixture screening temp. ° C | Yield of BHET parts (% theory) | M.Pt. ° C | Yield of oligomer & filter-aid parts |
|---|---|---|---|---|---|---|---|---|---|---|
| 2 | 194 | 496 | NaHCO$_3$ 0.5 MnAc$_2$ 0.05 | ~20 | ~60 | 112 | 90–95 | 215(84.5%) | | 21.7 |
| 3 | 194 | 496 | KHCO$_3$ 1.0 | ~20 | ~78 dropping to ~70 | ~110 | 90–95 | 225(88.6% | | 12.7 |
| 4 | 194 | 496 | K$_2$CO$_3$ 0.65 | ~20 | ~60 | ~110 | 90–95 | 222.7(87.6%) | | 13.8 |
| 4A | 194 | 620 | K$_2$CO$_3$ 0.65 | ~20 | ~60 | ~110 | 90–95 | 239 (94.1%) | | 5.6 |
| 5 (oligomer from 1 added) | 194 | 496 | Na$_2$CO$_3$ 0.125 | ~50 | ~75 | ~120–125 | 90–95 | 229(90.2%) | 108.4–109.2 | 22.5 |
| 6 (oligomer from 5 added) | 194 | 496 | Na$_2$CO$_3$ 0.125 | ~50 | ~75 | ~120–125 | 90–95 | 225(88.6%) | 108.6–109.2 | 27 |
| 7 (oligomer from 6 added) | 194 | 496 | Na$_2$CO$_3$ 0.125 | ~50 | ~75 | ~120–125 | 90–95 | 245(96.5%) | 108.8–110.0 | 19 |
| 8 (oligomer from 7 added) | 194 | 496 | Na$_2$CO$_3$ 0.125 | ~50 | ~75 | ~120–125 | 90–95 | 231(91%) | 108.8–109.8 | 28 |
| 9 | 194 | 620 | Na$_2$CO$_3$ 0.5 | ~20 | ~65-70 | ~110 | ~100 | 232.4(91.6%) | 108.8–110.4 | 5.5 |
| 10 | 194 | 496 | Na$_2$HPO$_4$ 1.34 | ~20 | ~80 | ~110–115 | 70–75 | 201.5(79.3%) | 109.6–110.2 | 32 |
| 11 | 194 | 496 | Na$_2$CO$_3$ 0.5 MnAc$_2$ 0.025 | ~20 | ~65-70 | ~110 | 70–75 | 202.5(79.7%) | 109.8–110.2 | 34.9 |
| 12 | 97 | 248 | CH$_2$COOH 1.5 NaHCO$_3$ 2.0 added | atm | almost no reaction | | ~90–95 | 91.5(72%) | — | — |
| 13 | 97 | 248 | MnAc$_2$ 0.025 H$_2$SO$_4$ 1.0 ml. | atm | First 40 ml. distillate 7%H$_2$O Second 20 ml. distillate 61% H$_2$O | — | — | — | — | — |
| 14 | 97 | 248 | MnAc$_2$ 0.025 H$_2$SO$_4$ 1.0 ml. NaHCO$_3$ 3.2 added | atm | First 22 ml. distillate 8.35% H$_2$O Second 22 ml. distillate 17.92% H$_2$O | | 90–95 | 65.2(51.4%) | | 8 |
| 15 | 194 | 496 | MnAc$_2$ 0.05 | atm | 150 | 200 | 90–95 | 178(70%) | 108–110 | — |
| 16 | 194 | 496 | MnAc$_2$ 0.05 | 20 | no reaction | | | | | |
| 17 | 194 | 496 | MnAc$_2$ 0.5 | 200 | ~130 | ~170 | 90–95 | 190(74.8%) | | 23.9 |
| 17A Note 1 | 194 | 496 | MnAc$_2$ 0.05 | 70 | 115 | 126 | 90–95 | 215(84.7%) | | 4.8 |
| 18 | 194 | 496 | 32% aqueous NaOH 0.29 | 20 | ~72 | ~110 | 90–95 | 211(83.2%) | 109.8–111.0 | 25 |
| 19 | 194 | 496 | Benzyl trimethyl ammonium | 20 | ~72 | ~110 | 90–95 | 213(83.8) | 109.4–110.4 | 21 |

TABLE I-continued

| Example No. | DMT Wt. parts | EG Wt. parts | Catalyst parts | mm Hg. Vacuum | Temperature of start of reaction °C | Maximum temp. of reaction mixture °C | Drown-out mixture screening temp. °C | Yield of BHET parts (% theory) | M.Pt. °C | Yield of oligomer & filter-aid parts |
|---|---|---|---|---|---|---|---|---|---|---|
| 20 | 194 | 496 | hydroxide 40% 1.0 CaO 0.3 | 15–20 | ~65 | ~105 | 95 | 220(86.6) | | 12.7 |
| 20A | 194 | 496 | Ba(OH)₂ | ~20 | ~65 | ~105 | 95 | 226.3(89.2) | 107.5—109 | 10 |

In this table
MnAc₂ = manganese acetate tetrahydrate,
BHET = bis-(2-hydroxyethyl)-terephthalate,
DMT = dimethyl terephthalate,
EG = ethylene glycol.
Note 1. DMT recrystallised from toluene, EG redistilled and MnAc₂ dried before weighing.

Example 21

In this example, the ethylene glycol has a free acidity (expressed as % - COOH) less than 0.0013% and that of the dimethyl terephthalate was 0.03%. The acidity in 194 parts of dimethyl terephthalate was therefore equivalent to 0.068 parts of sodium carbonate.

This example was carried out as described in Example 1, the reaction vessel being charged with the above analysed ethylene glycol (496 parts) and dimethyl terephthalate. Instead of adding solid sodium carbonate directly, a solution was made containing 0.1 part in ethylene glycol (25 parts by volume). This solution was placed in a burette which was fitted into a suitable vacuum-tight inlet in the reaction vessel. The mixture in the reaction vessel was heated to approximately 70°–75° C and the solution of sodium carbonte in ethylene glycol was added dropwise until 13.5 parts by volume had been added, when methanol began to distil. The theoretical volume of sodium carbonate required to neutralise the free acidity of the DMT was 13.6 parts by volume agreeing well, within the experimental limits, with that actually used before reaction began. The reaction continued normally and a yield of 208 parts (81.9%) of bis-(2-hydroxyethyl)-terephthalate was obtained m.pt. 108.4 – 109.8° C. The oligomer residue weighed 14.5 parts.

Example 22

In this example, the reaction was carried out as in Example 1 except that the quantity of sodium carbonate used was increased to 0.5 parts and the source of vacuum was an oil pump protected by two solid carbon dioxide vapour traps and giving a vacuum of 0.5 – 1.0 mm Hg. The mixture was heated and methanol began to distil out of the system at about 50°– 55° C. Reaction continued as in Example 1 but as the reaction mixture temperature rose, dimethyl terephthalate began to sublime out of the system into the condenser and receiver system. When the reaction was complete the product was isolated as described in Example 1. The yield of bis-(2-hydroxyethyl)-terephthalate was 196.3 parts (77.2%) and the oligomer residue weighed 49.4 parts inclusive of filter-aid.

Example 23

A. The apparatus used was similar to that of Example 1. The reaction flask was charged with dimethyl terephthalate (194 parts), ethylene glycol (1240 parts) and sodium carbonate (0.125 part). The apparatus was evacuated to 20–30 mm. Hg. and the mixture was heated. Methanol distilled out of the system and was condensed using methanol cooled by solid carbon dioxide (yield of methanol 80.5 parts by volume, = 65 parts by weight, s.g. = 0.807, theory weight = 64 parts s.g. 0.78 approximately).

The reaction was allowed to cool with slow agitation to 20° C. When crystallisation was complete, the bis-(2-hydroxyethyl)-terephthalate was filtered off using a vacuum filter. One displacement wash using ethylene glycol was given and then the filter cake was washed free of ethylene glycol using water. The product was dried at 55°–60° C. Yield 217 parts (85.4%) m.pt. 108.5°– 109.5° C. B. The glycol liquor from this preparation was re-used in a second preparation using the following proportions of reactants. Dimethyl terephthalate (108 parts, recovered ethylene glycol (700 parts), sodium carbonate (0.17 part, extra being used to allow for the increased acidity of the recovered ethylene glycol). The product was worked up in a similar manner to the first experiment. Yield 118 parts (83.4%), m.pt. 105°–106° C.

We claim:

1. A process for the manufacture of bis-(2-hydroxyethyl)-terephthalate, which comprises heating together dimethyl terephthalate and ethylene glycol, the molar ratio of ethylene glycol to dimethyl terephthalate being at least 8:1, under distillation conditions at a pressure of from 15 mm to 100 mms Hg in the presence of a basic catalyst, said basic catalyst being an alkali or alkaline earth metal or an oxide, hydroxide, stable bicarbonate, carbonate or alcoholate thereof or a quaternary ammonium hydroxide or a dialkali hydrogen phosphate, in excess over that required to neutralize any acidity in the dimethyl terephthalate or ethylene glycol.

2. A process as claimed in claim 1 wherein the molar ratio of ethylene glycol to dimethyl terephthalate is from 8:1 to 10:1

3. A process as claimed in claim 1 wherein the distillation conditions include a packed distillation column in order to assist separation of methanol and ethylene glycol.

4. A process as claimed in claim 1 wherein the amount of basic catalyst is from 0.025 to 1.0% by weight of the dimethyl terephthalate.

5. A process as claimed in claim 4 wherein the amount of basic catalyst is from 0.2 to 0.3% by weight.

6. A process as claimed in claim 1 wherein the bis-(2-hydroxyethyl)-terephthalate is isolated by pouring the reaction mixture into water, separating the hot aqueous liquor from insolubles and allowing the product to crystallise.

7. A process as claimed in claim 1 wherein the bis-(2-hydroxyethyl)-terephthalate is allowed to crystallise from the reaction liquid and is separated from the mother liquor which is then used in another preparation.

* * * * *